(12) United States Patent
Wang

(10) Patent No.: US 10,646,111 B2
(45) Date of Patent: May 12, 2020

(54) SPECTRALLY ENCODED ENDOSCOPY APPARATUS AND METHODS

(71) Applicant: Canon USA Inc., Melville, NY (US)

(72) Inventor: Zhuo Wang, Santa Clara, CA (US)

(73) Assignee: Canon U.S.A., Inc., Melville, NY (US)

( * ) Notice: Subject to any disclaimer, the term of this patent is extended or adjusted under 35 U.S.C. 154(b) by 69 days.

(21) Appl. No.: 15/713,233

(22) Filed: Sep. 22, 2017

(65) Prior Publication Data

US 2018/0084981 A1   Mar. 29, 2018

Related U.S. Application Data

(60) Provisional application No. 62/399,042, filed on Sep. 23, 2016.

(51) Int. Cl.
| | |
|---|---|
| *A61B 1/07* | (2006.01) |
| *G01B 9/02* | (2006.01) |
| *A61B 1/06* | (2006.01) |
| *A61B 1/00* | (2006.01) |
| *A61B 5/00* | (2006.01) |

(Continued)

(52) U.S. Cl.
CPC ............ *A61B 1/07* (2013.01); *A61B 1/00009* (2013.01); *A61B 1/00096* (2013.01); *A61B 1/00165* (2013.01); *A61B 1/00172* (2013.01); *A61B 1/00183* (2013.01); *A61B 1/00188* (2013.01); *A61B 1/0638* (2013.01); *A61B 5/0066* (2013.01); *G01B 9/0205* (2013.01); *G01B 9/02091* (2013.01); *G02B 23/2469* (2013.01); *G02B 23/26* (2013.01)

(58) Field of Classification Search
CPC ............ A61B 1/00009; A61B 1/00096; A61B 1/00165; A61B 1/00172; A61B 1/00188; A61B 1/0638; A61B 1/07; A61B 5/0066; G01B 9/0205; G01B 9/02091; G02B 23/2469; G02B 23/26

See application file for complete search history.

(56) References Cited

U.S. PATENT DOCUMENTS

| | | |
|---|---|---|
| 3,976,360 A | 8/1976 | Schroder |
| 4,074,306 A | 2/1978 | Kakinuma et al. |
| 4,264,127 A | 4/1981 | Schumacher et al. |

(Continued)

FOREIGN PATENT DOCUMENTS

| | | |
|---|---|---|
| WO | 2007/084903 A2 | 7/2007 |
| WO | 2014031748 A1 | 2/2014 |

(Continued)

OTHER PUBLICATIONS

Singh, K., et al, "Common Path Side Viewing Monolithic Ball Lens Probe for Optical Coherence Tomography", STM, 2015, pp. 29-33, vol. 7, No. 1.

(Continued)

*Primary Examiner* — Michael A Lyons
(74) *Attorney, Agent, or Firm* — Canon U.S.A., Inc. IP Division

(57) ABSTRACT

An apparatus, method, and system for a spectrally encoded endoscope comprising a focusing lens encompassed by an light guiding component and spacer, wherein the focusing lens is substantially ball or semi-circular in shape, and the refractive index of the focusing lens is greater than the refractive index of the spacer.

19 Claims, 11 Drawing Sheets

(51) Int. Cl.
*G02B 23/24* (2006.01)
*G02B 23/26* (2006.01)

(56) References Cited

U.S. PATENT DOCUMENTS

| | | |
|---|---|---|
| 5,279,280 A | 1/1994 | Bacich et al. |
| 5,565,983 A | 10/1996 | Barnard |
| 5,909,529 A | 6/1999 | Bhagavatula |
| 6,327,493 B1 | 12/2001 | Ozawa et al. |
| 6,341,036 B1 | 1/2002 | Tearney et al. |
| 6,370,422 B1 | 4/2002 | Richards-Kortum et al. |
| 6,485,413 B1 | 11/2002 | Boppart et al. |
| 6,661,513 B1 | 12/2003 | Granger |
| 6,831,781 B2 | 12/2004 | Tearney et al. |
| 6,858,859 B2 | 2/2005 | Kusunose |
| 6,862,383 B2 | 3/2005 | Kikuchi et al. |
| 7,003,196 B2 | 2/2006 | Ghiron |
| 7,262,923 B2 | 8/2007 | Quake et al. |
| 7,342,659 B2 | 3/2008 | Horn et al. |
| 7,448,995 B2 | 11/2008 | Wiklof et al. |
| 7,647,092 B2 | 1/2010 | Motz et al. |
| 7,796,270 B2 | 9/2010 | Yelin et al. |
| 7,843,572 B2 | 11/2010 | Tearney et al. |
| 7,859,679 B2 | 12/2010 | Bouma et al. |
| 3,045,177 A1 | 10/2011 | Tearney et al. |
| 8,145,018 B2 | 3/2012 | Shishkov et al. |
| 8,203,708 B2 | 6/2012 | Lee et al. |
| 8,285,368 B2 | 10/2012 | Chen et al. |
| 8,289,522 B2 | 10/2012 | Tearney et al. |
| 8,780,176 B2 | 7/2014 | Yelin |
| 8,804,133 B2 | 8/2014 | Yelin et al. |
| 8,812,087 B2 | 8/2014 | Yelin et al. |
| 8,818,149 B2 | 8/2014 | Shishkov et al. |
| 8,838,213 B2 | 9/2014 | Tearney et al. |
| 9,057,594 B2 | 6/2015 | Kang et al. |
| 9,254,089 B2 | 2/2016 | Tearney et al. |
| 9,683,928 B2 * | 6/2017 | Swanson ............ A61B 5/0066 |
| 2002/0114566 A1 | 8/2002 | Fairchild et al. |
| 2002/0145815 A1 | 10/2002 | Moriyama et al. |
| 2003/0142934 A1 | 7/2003 | Pan et al. |
| 2004/0147810 A1 | 7/2004 | Mizuno |
| 2005/0155704 A1 | 7/2005 | Yokajty et al. |
| 2007/0188855 A1 | 8/2007 | Shishkov et al. |
| 2007/0233396 A1 | 10/2007 | Tearney et al. |
| 2007/0276187 A1 | 11/2007 | Wiklof et al. |
| 2008/0013960 A1 | 1/2008 | Tearney et al. |
| 2008/0097225 A1 | 4/2008 | Tearney et al. |
| 2008/0228033 A1 | 9/2008 | Tumlinson et al. |
| 2009/0141360 A1 | 6/2009 | Koyama |
| 2009/0153932 A1 | 6/2009 | Davis et al. |
| 2009/0284749 A1 * | 11/2009 | Johnson ............ A61B 5/0066 356/497 |
| 2010/0210937 A1 | 8/2010 | Tearney et al. |
| 2011/0237892 A1 | 9/2011 | Tearney et al. |
| 2011/0275899 A1 | 11/2011 | Tearney et al. |
| 2012/0112094 A1 | 5/2012 | Kao et al. |
| 2012/0212595 A1 | 8/2012 | Parmar et al. |
| 2012/0243251 A1 | 9/2012 | Suzuki et al. |
| 2013/0012771 A1 | 1/2013 | Robertson |
| 2014/0037245 A1 * | 2/2014 | Sinclair ............ A61B 5/0082 385/33 |
| 2014/0153864 A1 | 6/2014 | Sinclair et al. |
| 2014/0160482 A1 | 6/2014 | Tearney et al. |
| 2014/0285878 A1 | 9/2014 | Escuti et al. |
| 2014/0378846 A1 | 12/2014 | Hosoda et al. |
| 2015/0045622 A1 | 2/2015 | Shishkov et al. |
| 2015/0131098 A1 | 5/2015 | Yang et al. |
| 2015/0253240 A1 | 9/2015 | Rowe et al. |
| 2015/0335248 A1 | 11/2015 | Huang et al. |
| 2016/0341951 A1 * | 11/2016 | Tearney ............ A61B 1/00096 |
| 2018/0045501 A1 * | 2/2018 | Elmaanaoui ....... G01B 9/02015 |

FOREIGN PATENT DOCUMENTS

| | | |
|---|---|---|
| WO | 2014104405 A1 | 7/2014 |
| WO | 2014121389 A1 | 8/2014 |
| WO | 2015/042093 A1 | 3/2015 |
| WO | 2015116939 A1 | 8/2015 |
| WO | 2015116951 A2 | 8/2015 |
| WO | 2015116974 A1 | 8/2015 |
| WO | 2017/024145 A1 | 2/2017 |

OTHER PUBLICATIONS

Zeidan, A et al. "Miniature forward-viewing spectrally encoded endoscopic probe", Optics Letters, Aug. 15, 2014, pp. 4871-4874, vol. 39, Issue 16.

Pitris, C. et al., "A GRISM-based probe for spectrally encoded confocal microscopy" Optics Express, Jan. 27, 2003, pp. 120-124, vol. 11, No. 2.

Yelin, D., et al., "Three-dimensional miniature endoscopy", Nature, Oct. 19, 2006, p. 765, vol. 443.

Kang, D., et al., "Minature grating for spectrally-encoded endoscopy", Lab Chip, 2013, pp. 1810-1816, vol. 13.

Kang, D., et al., "Spectrally-encoded color imaging", Optics Express, Aug. 17, 2009, pp. 15239-15247, vol. 17, No. 17.

Moharam, M.G., et al, "Formlation for stable and efficient implementation of the rigorous coupled-wave analysis of binary gratings", J. Opt. Soc. Am. A, May 1995, pp. 1068-1076, vol. 12, No. 5.

Yun, et al., "High-speed spectral-domain optical coherence tomography at 1.3 μm wavelength", Opt Express, Dec. 29, 2003, pp. 3598-3604, No. 11, vol. 26.

Tearney, G.J., et al., "Spectrally encoded miniature endoscopy", Optics Letters, Mar. 15, 2002, pp. 412-414, vol. 27, No. 6.

Bai, B., et al. "Optimization of nonbinary slanted surface-relief gratings as high-efficiency broadband couplers for light guides", Applied Optics, Oct. 1, 2010, pp. 5454-5464, vol. 49, No. 28.

Barlev, O., et al., "Design and experimental investigation of highly efficient resonance-domain diffraction gratings in the visible spectral region", Applied Optics, Dec. 1, 2012, pp. 8074-8080, vol. 51, No. 34.

"OFS Announces Successful Splice of Sapphire and Silica Optical Fibers", CISION PR Newswire, Feb. 5, 2013; http://www.prnewswire.com/news-releases/ofs-announces-successful-splice-of-sapphire-and-silica-optical-fibers-189784631.html.

Barnes, A.E., et al, "Sapphire fibers: optical attenuation and splicing techniques", Applied Optics, Oct. 20, 1995, pp. 6855-6858, vol. 34, No. 30.

Merberg, G.N., et al, "Optical and mechanical properties of single-crystal sapphire optical fibers", Applied Optics, Jun. 20, 1993, pp. 3201-3209, vol. 32, No. 18.

Jundt, D.H., et al, "Characterization of single-crystal sapphire fibers for optical power delivery systems", Appl. Phys. Lett., Nov. 20, 1989, pp. 2170-2172, vol. 55, No. 21.

* cited by examiner

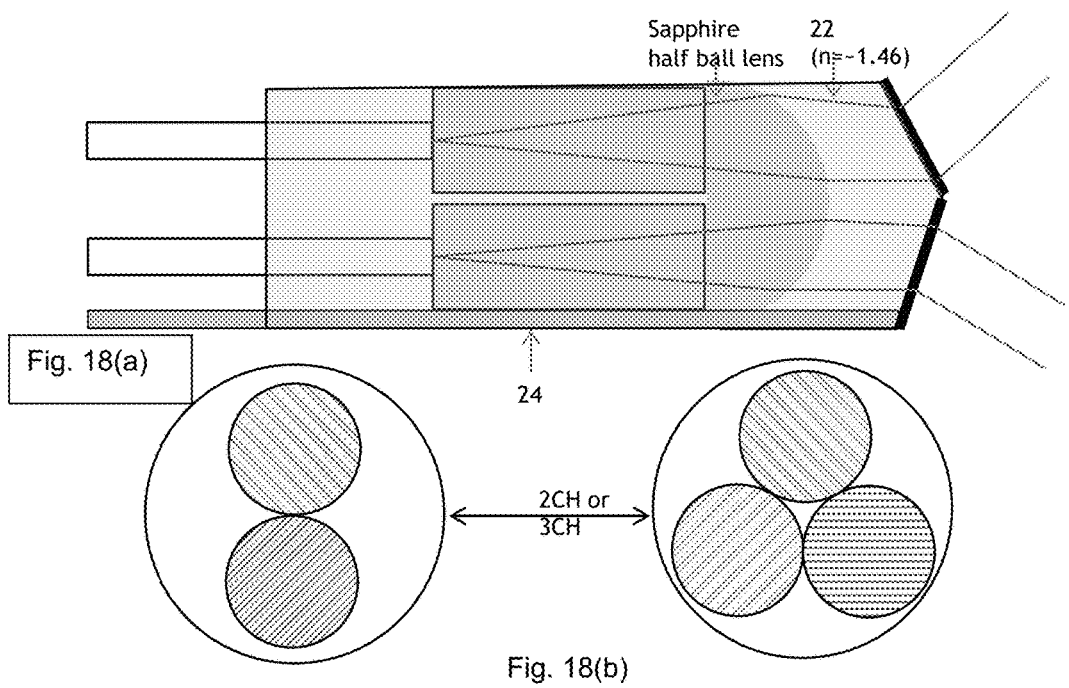
Fig. 18(a)
Fig. 18(b)
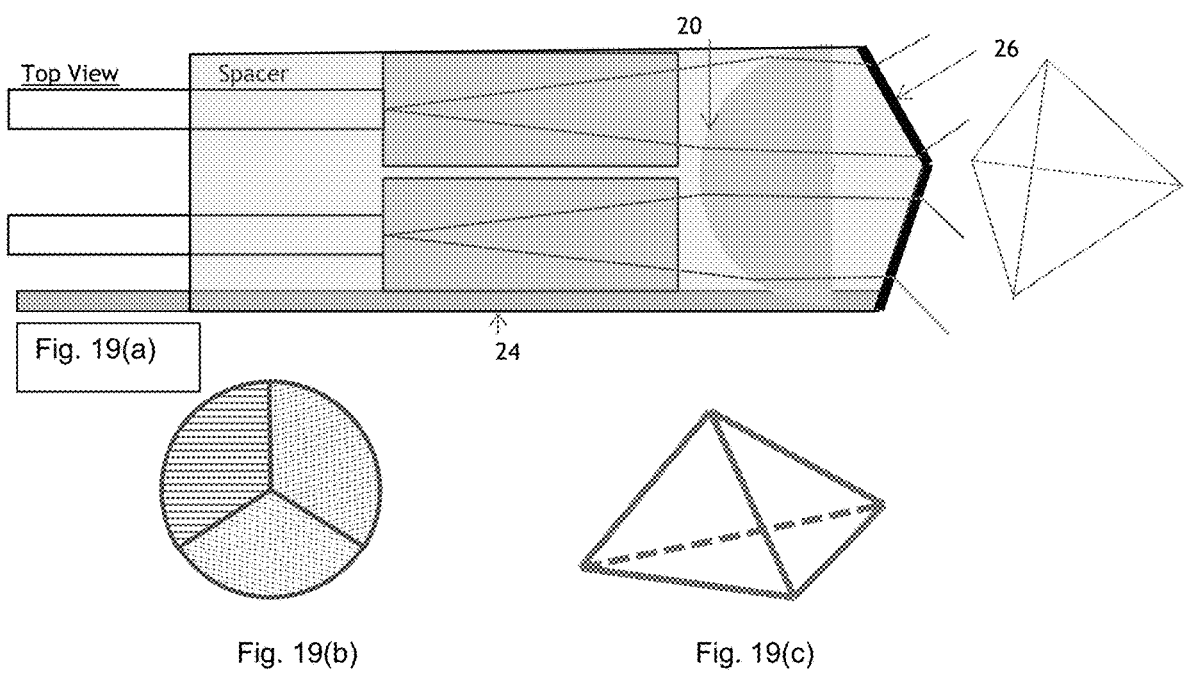
Fig. 19(a)
Fig. 19(b)        Fig. 19(c)

SPECTRALLY ENCODED ENDOSCOPY APPARATUS AND METHODS

CROSS-REFERENCE TO RELATED APPLICATIONS

This application claims priority to U.S. Provisional Application Ser. No. 62/399,042 filed 23 Sep. 2016, the content of which is incorporated herein by reference in its entirety.

FIELD OF THE DISCLOSURE

The present disclosure relates generally to apparatus and methods for endoscopy and for obtaining information having a sandwiched ball lens, as well as methods for manipulating the apparatus, and methods for manufacturing the endoscope.

DESCRIPTION OF THE RELATED ART

Medical probes have the ability to provide images from inside a patient's body. Considering the potential harm capable to the human body caused by the insertion of a foreign object, it is preferable that the probe be as small as possible. Additionally, the ability to provide images within small pathways such as vessels, ducts, incisions, gaps and cavities dictates the use of a small probe.

One particularly useful medical probe is the spectrally encoded endoscopy ("SEE"), which is a miniature endoscope that can conduct high-definition imaging through a sub-mm diameter probe. At the heart of the SEE system lays the SEE probe, of which an example is provided in FIG. 1. In operation, light from an light guiding component found in the SEE probe, (single mode fiber ("SMF") usually for better resolution) is first coupled into a coreless fiber and then into a Gradient Index ("GRIN") lens and focused on the sample to be analyzed. Light reflected by the sample is captured by a detection fiber (i.e. spectrometer) and imaged for viewing. Epoxies may be used to glue the coreless fiber with the GRIN lens. The coreless fiber is spliced with the single mode fiber to decrease the light intensity inside the epoxy as the extremely high light intensity inside the single mode fiber tends to yellow and even burn the epoxy after running for an extended period of time.

Although very useful, the current SEE probe presents several issues associated with the sample provided in FIG. 1. Firstly, the cost of the GRIN lens is very high, and consequently leads to stunted widespread use and adoption of the probe. Secondly, the design of the GRIN lens requires the side surfaces to be fine polished which introduces additional labor cost, as well maintenance and care concerns. Third, a GRIN lens has very large color aberrations which degrade the imaging quality in both the blue and red end of the spectrum. Fourth, the joint between the GRIN lens and the coreless fiber is weak, which leads to potential failures and limited use of the GRIN lens in constricted areas. Last but not least, the GRIN lens is not flexible at all. The current design the GRIN lens is in the range of 3 to 4 mm, which means the 3 to 4 mm SEE tip is rigid. This can be problematic when the probe needs to be inserted into smaller curved lumens or cavities.

Several solutions have been contemplated to address the issues referenced above in curing handicaps of the current SEE system.

Alternatively, the advent of the air-spaced ball lens has been proposed to focus light in place of the GRIN lens. However, the ball lens has only been used for optical focusing purpose. In the current art, no mechanical support of the ball lens is possible, as the current designs require an air-gap after the lens. Conversely, mechanical support is critical for a SEE probe as the dispersion element after the focusing element whose relative position to the ball lens needs to be fixed properly. As a result, an additional support has been suggested to retain the mechanical integrity. However other factors have reduced the value of this solution, as the required air-gap also leads to additional light loss due to scattering. The air-gap between the ball lens and the SMF also serves the purpose of introducing a large refractive index difference so that the light will be reflected as the reference beam. If a refractive index matching medium is introduced at this interface, it is difficult to have a reference beam available.

Similarly, it is possible to form the ball lens on the tip of a SMF and thus improve the reliability. However, as before, one needs the air-ball lens interface to introduce a large refractive index contrast so that light can be reflected to form the reference signal. Additional support is again suggested to hold the ball lens and the prism, which doesn't resolve the scattering issue, and further complicates and introduces difficulties in the assembly stage.

Accordingly, it is particularly beneficial to disclose a new SEE system, apparatus and methods that benefits from: lower cost to manufacture, operate and maintain; lower color aberrations which cause image degradation; greater optimization of image quality; robust connectivity of the SEE probe; and flexibility in the SEE tip for enhanced mobility through small lumens.

SUMMARY OF EXEMPLARY EMBODIMENTS

Thus, to address such exemplary needs, the presently disclosed apparatus, systems, and methods for a SEE having a sandwiched ball lens are provided herein.

The present disclosure teaches various apparatus for spectrally encoded endoscopy comprising a probe for illuminating a sample, wherein the probe comprises a light guiding component for guiding an illumination light, a light focusing component, a spacer; and a dispersive component. The apparatus optionally further comprises a light guiding component for guiding light reflected from the sample, wherein the spacer encompasses at least the light focusing component, thus eliminating any air gap between the spacer and light focusing component. In some embodiments, the light guiding component for guiding the illumination light and the light guiding component for guiding light reflected from the sample (i.e., detected light) are a single optical fiber; in other embodiments, separate optical fibers are used.

The present disclosure also teaches an apparatus for endoscopy comprising a probe for illuminating a sample, wherein the probe comprises a light guiding component for guiding an illumination light, a light focusing component, a spacer; and a dispersive component. The apparatus optionally further comprise a separate light guiding component (e.g., a detection fiber) for guiding light from the sample. The spacer has a refractive index that is less than a refractive index of the light focusing component.

In addition, the present disclosure teaches an apparatus for optical coherence tomography or other endoscopy imaging modalities comprising a probe for illuminating a sample, wherein the probe comprises a light guiding component for guiding an illumination light, a light focusing component, a reflective component, and a spacer. The spacer encompasses at least the light focusing component, thus eliminating any air gap between the spacer and light focusing component.

Furthermore, the present disclosure teaches an apparatus for optical coherence tomography or other endoscopy imaging modalities comprising a probe for illuminating a sample, wherein the probe comprises a light guiding component for guiding an illumination light, a light focusing component, a spacer; and a reflective component. The spacer has a refractive index less than a refractive index of the light focusing component.

In various embodiments, the spacer has a refractive index that is less than a refractive index of the light focusing component.

In another embodiment, the apparatus comprises a rod, situated between the light guiding component and light focusing component, such that the rod is configured to expand light sourced from the probe.

In one or more embodiments, the apparatus may enact a refractive index of the rod being equal to or higher than a refractive index of the light guiding component.

In other embodiments of the apparatus, the difference of the refractive index of the light focusing component and that of the spacer is greater than or equal to 0.05.

In yet another embodiment, the spacer is configured to at least partially encompasses the light guiding component.

In some embodiments, the spacer provides support for the light focusing component, and the spacer may be formed by immersing the light focusing element into a hollow cylinder containing liquid PDMS. In various additional embodiments, the PDMS forming the spacer may be in contact with a grating. In certain embodiments, the hollow cylinder may be removed once the liquid PDMS has hardened, or the PDMS may remain as a protective element. In yet further embodiments, the cylinder may comprise of one, two or three piece molds.

In another embodiment, the light focusing component is selected from the group comprising a ball lens, a half-ball lens, a portioned-ball lens (usually formed by grinding a full ball lens to certain thickness that is not exactly half of the lens diameter), a lens with a spherical surface, a lens with aspherical surface, derivatives thereof and combinations therefrom. A flat surface is considered spherical with the radius equals to infinity.

In another embodiment of the present disclosure, light focusing component is at least partially made of an element selected from the group comprising, sapphire, ruby, flint glass, derivatives thereof and combinations therefrom.

In another embodiment, the light focusing component is at least partially formed by an injected molded lens having a spherical shape or aspherical shape.

In certain embodiments, the apparatus may further comprise a rod diameter equal to or greater than a diameter of the light guiding component.

In yet additional embodiments, the apparatus may further comprise a focusing element for tuning the focus of the probe by varying a refractive index of the spacer:

In another embodiment of the subject disclosure, the apparatus further comprises a computer arrangement in communication with the apparatus, and configured to process information received from the apparatus to create an image.

In yet an additional embodiment, the subject apparatus teaches attachment of the light guiding component, light focusing component, and rod utilizing adhesives, splicing, derivatives thereof and combinations therefrom.

In yet another embodiment, two or more detection fibers may be incorporated into the apparatus. The detection fibers may be configured around the light focusing component (e.g., 4 to 12 fibers arranged concentrically around the light focusing component.)

In one or more embodiments of the apparatus, the spacer material is at least partially made of an element selected from the group comprising UV or heat cured epoxies, PDMS (silicone), PMMA, PC, injection moldable glass, derivatives thereof and combinations therefrom.

In certain embodiments of the subject apparatus, the spacer may incorporate a polished, angled tip for redirecting light generated by the light guiding component.

In other embodiments of the subject apparatus, two or more light guiding elements may be incorporated, wherein the two or more light guiding elements utilize a single light focusing element. In certain embodiments, the spacer may incorporate two or more separate gratings at one of the spacer.

In yet other embodiments, the spacer of apparatus described herein above is formed by immersing the focusing element into a liquid such as PDMS. The liquid may be in a cylinder which can be a two piece mold or three piece mold, and may be a part of the protective sheath. During the formation of the spacer, one side of PDMS can be contacted with a master grating to form the grating surface for SEE or alternatively be fabricated having a flat surface for OCT and other endoscopic applications. The PDMS is thermally cured, such as by placing the spacer in an oven. An additional curvature on the distal end of the probe can be molded as well.

These and other objects, features, and advantages of the present disclosure will become apparent upon reading the following detailed description of exemplary embodiments of the present disclosure, when taken in conjunction with the appended drawings, and provided paragraphs.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIGS. 18(a) and 18(b) provides a schematic diagram of an exemplary SEE probe featuring a shared ball lens utilized for color imaging (FIG. 18(a)) and the two or 3 channel color configuration (FIG. 18(b), according to one or more embodiments of the present subject matter.

FIGS. 19(a), 19(b) and 19(c) provides a schematic diagram of an exemplary SEE probe featuring a shared ball lens utilized for color imaging (FIG. 19(a)) with the grating (FIG. 19(b)) and a pyramid tip to increase the surface area (FIG. 19(c)), according to one or more embodiments of the present subject matter.

Figure 1:
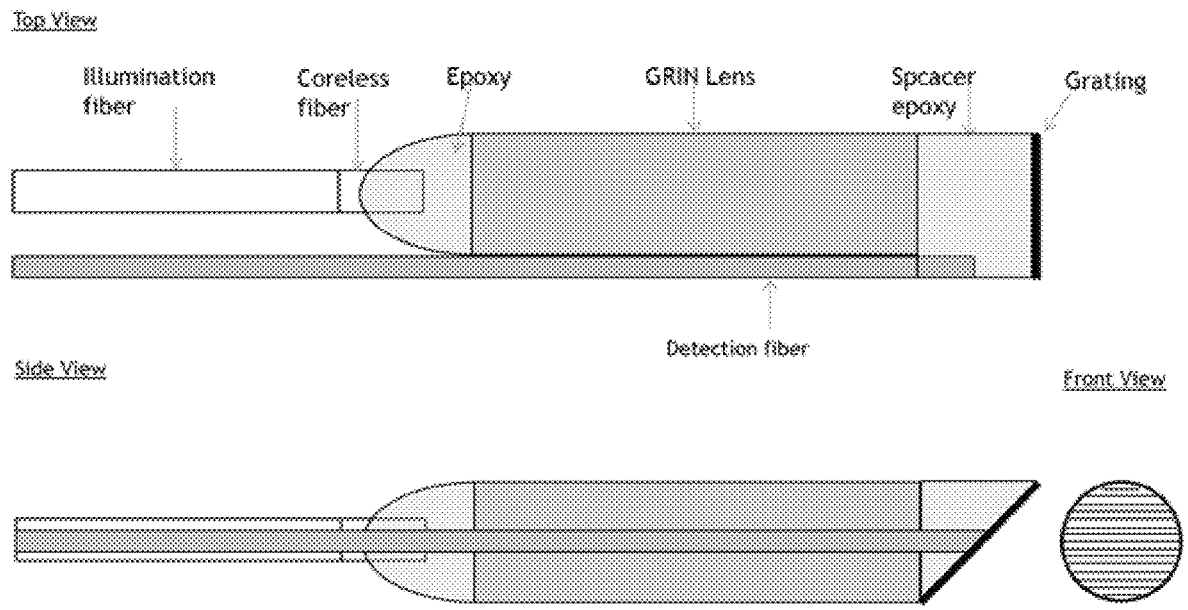
FIG. 1 depicts several views of a spectrally encoded endoscope probe GRIN Lens with accompanying components typical of the prior art.

Throughout the Figures, the same reference numerals and characters, unless otherwise stated, are used to denote like features, elements, components or portions of the illustrated embodiments. In addition, reference numeral(s) including by the designation "'" (e.g. 12' or 24') signify prior art elements and/or references. Moreover, while the subject invention will now be described in detail with reference to the Figures, it is done so in connection with the illustrative embodiments. It is intended that changes and modifications can be made to the described embodiments without departing from the true scope and spirit of the subject disclosure as defined by the appended paragraphs.

DETAILED DESCRIPTION OF EXEMPLARY EMBODIMENTS

FIG. 1 depicts a spectrally encoded endoscope probe incorporating a GRIN lens with accompanying components typical of the prior art. The light guiding component (single mode fiber usually for better resolution) is coupled into the coreless fiber and then attached to the GRIN (Gradient Index) lens for focusing purpose. Epoxies are typically used to glue the coreless fiber with the GRIN lens. The coreless fiber may be spliced with the SMF (single mode fiber) which is used to decrease the light intensity inside of the epoxy, as the extremely high light intensity inside the SMF tends to yellow and even burn the epoxy after operating the probe for an extended period of time. As provided earlier, the deficient elements of this prior art system are the cost associated with the GRIN lens, the lack of flexibility in the GRIN lens, as well as the fragility of the epoxy joints. As mentioned before, the yellowing of the epoxy is an additional detriment.

As depicted in FIG. 1, SEE probes often use a grating at the tip of the probe where broadband light is diffracted, producing a dispersed spectrum on the sample to be imaged. Light returned from the sample is detected using a detection fiber (e.g. spectrometer), and each resolvable wavelength corresponds to reflectance from a different point on the sample. The principle of the SEE technique and SEE probe, having a diameter of 0.5 mm, i.e., 500 µm, has been reported by D. Yelin et al. [(Nature Vol. 443, 765-765 (2006)], which is incorporated by reference in its entirety herein.

Alternatives to the prior art provided in FIG. 1 have been contemplated, including disclosures presented in U.S. Pat. No. 9,057,594, U.S. Pat. No. 8,145,018, and others. However, the ball lens contemplated in the prior art is only used for optical focusing purposes. No mechanical support is possible with this design as there is always an air-gap after the lens. As mechanical support is advantageous for SEE systems, as the dispersion element is after the focusing element whose relative position to the ball lens needs to be fixed properly, additional support is suggested to retain the mechanical integrity, which is at the expense of increased diameter and complexity. The air-gap between the ball lens and the SMF also serves the purpose of introducing a large refractive index difference so that the light may be reflected as the reference beam. If a refractive index matching medium is introduced at this interface, it is difficult to have a reference beam available. Assembly and reliability are concern in the prior art, as the ball lens is not directly connected to the SMF. Additionally, air-gaps introduce more light loss from scattering, further diminishing utility.

Figure 5:
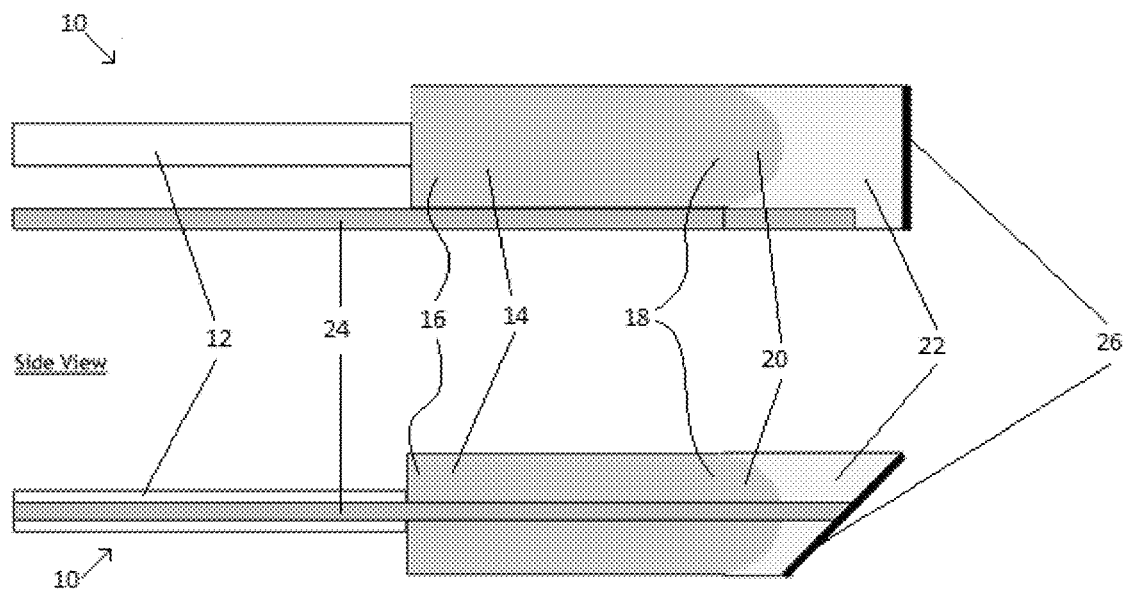
FIG. 5 depicts a top and side view of a schematic diagram of an exemplary SEE probe, incorporating a monolithic design.

In FIG. 5 we depict an exemplary embodiment of the subject disclosure of a SEE probe 10, incorporating a monolithic design, according to one or more embodiments of the present subject matter. As depicted, the probe comprises a light guiding component 12 spliced to a proximal end 16 of a glass rod 14. A distal end 18 of the glass rod 14 is attached to a ball lens 20 (also referred to as a "light focusing component"), wherein a spacer 22 is molded to the ball lens 20. Accordingly, the assembly produces the ball lens 20 at least partially encompassed by the spacer 22, thus eliminating the problematic air-gap seen in the prior art. In this embodiment the ball lens 20 has a refractive index greater than the refractive index of the spacer 22. A detection fiber 24 is also configured to detect reflected light from the sample (not shown) which is illuminated by the SEE probe 10. The material for the glass rod 14 can be similar to the light guiding component 12, which is also desired if one would like to splice the light guiding component 12 to the glass rod 14 with different diameters. As the light guiding component 12 is usually made of fused silica, it might be necessary for the spacer 22 to have a lower refractive index of 1.4 or even lower. The material selection of the spacer 22 is limited in this instance. The diameter of the ball lens 20 in this case is similar to the diameter of the glass rod 14. The diameter of the light guiding component 12 and the glass rod 14 can be similar or different. A larger glass rod 14, as shown here, is preferred when the divergent beam sourced from the SMF is required to be expanded before it contacts the ball lens 20.

Figure 6:
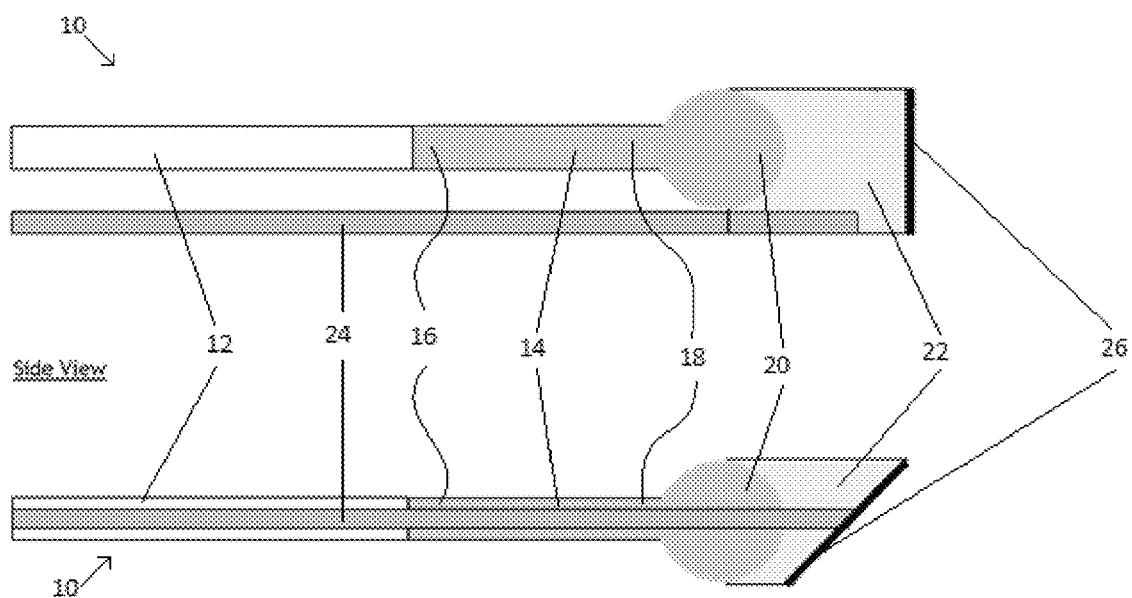
FIG. 6 illustrates a top and side view of a schematic diagram of an exemplary SEE probe featuring a light guiding component and rod having similar diameters, according to one or more embodiments of the present subject matter.

Alternatively, the glass rod 14 and the light guiding component 12 may be of similar diameters, thereby the light guiding component 12 can be spliced to the glass rod 14 of different materials as shown in FIG. 6. In this embodiment, one can choose the material for the glass rod 14 to be of a higher refractive index such as 1.6 or even higher (e.g. 1.77 for sapphire). Accordingly, the spacer 22 can then be made with typical silicones, epoxies or PMMAs. It is even possible to use polycarbonates if sapphire glass rod is used.

Alternatively, noting that for this embodiment, as long as one can splice the light guiding component 12 to the glass rod 14, it is not necessary to keep the size of the light guiding component 12 and the glass rod 14 the same. A factor of 5 or less, (i.e. if the SMF's diameter is 125 um, the upper limit of the glass rod will be 625 um) may be beneficial to accomplish a strong binding.

Furthermore, the spacer 22 may be extended onto the spliced joint 30 or 32 (not shown) or even covering part of the light guiding component 12 to facilitate the fabrication and/or improve the durability and strength of the SEE probe 10. In addition a grating 26 (also referred to as a "dispersion component") may be configured (etched or otherwise) at the end of the spacer 22 for diffracting light.

The detection fiber collects light reflected from the sample. The detection fiber can be one or more multi-mode fibers. The multiple fibers can be, for example, arrayed around the light focusing component and spacer. In some embodiments, there are 2, 3, 4, 5, 6, 7, 8, or more detection fibers. In some embodiments, the array of detection fibers can have a "hole" at one or more positions to accommodate other optical or mechanical components such as a flushing means. The detection fiber can be stationary or rotate with the light focusing component and spacer together. Preferably the detection fiber has a high NA. The NA can be more than 0.2. (more preferably . . . 0.3, 0.4, 0.5, 0.6, 0.7, 0.8, 0.9, etc.).

Figure 7:
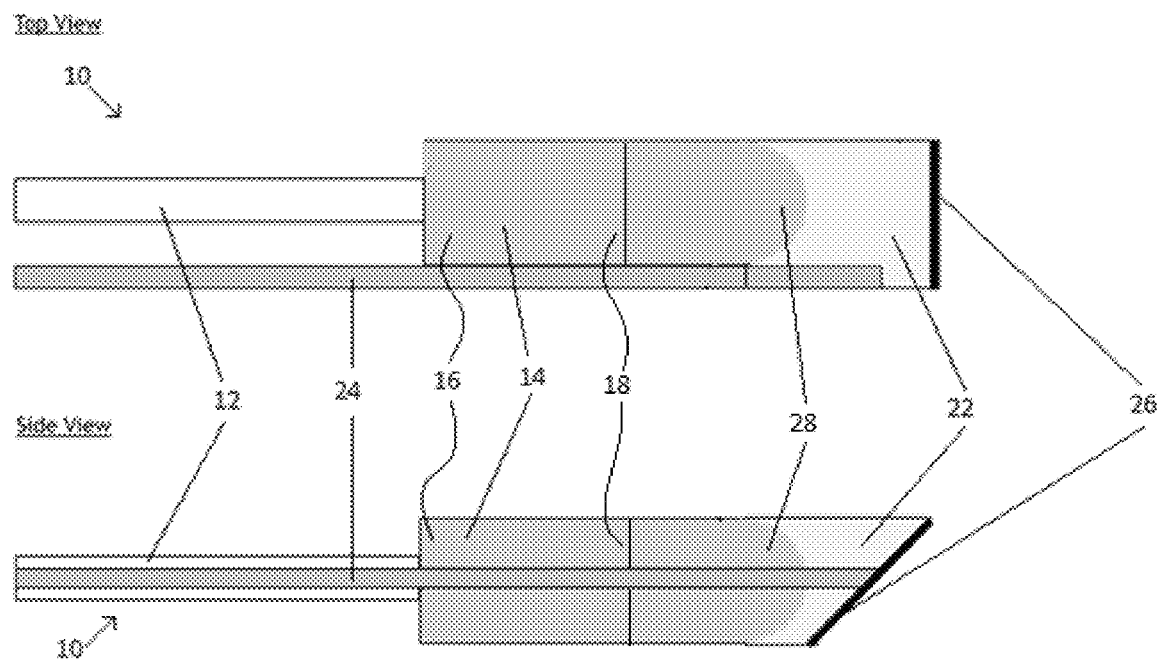
FIG. 7 illustrates a top and side view of a schematic diagram of an exemplary SEE probe featuring an injection molded aspherical lens, according to one or more embodiments of the present subject matter.

FIG. 7 illustrates yet another embodiment of an exemplary SEE probe 10 featuring an injection molded aspherical lens 28, according to one or more embodiments of the present subject matter. In this embodiment, an injected molded aspherical lens 28 is utilized. In various circumstances, a simple spherical surface may not be enough to correct aberrations in a SEE system. In order to properly correct aberrations (e.g. spherical aberration), it is possible to introduce the injection molded spherical and aspherical 28 (preferred) lens as shown in FIG. 7. Exemplary material for such an embodiment may be polycarbonate, which has a refractive index of 1.59. For such an embodiment, the glass rod 14 may be glued to the injection molded lens 28 at the distal end 18 of the glass rod 14. Admittedly, the glue may be a weak link in the system as the glued joint is usually not as strong as the spliced joint. An advantage of such an embodiment includes the ease of correction for spherical aberrations as the aspherical surface is introduced, thus improve the imaging quality. As before, it is preferred that the refractive index of the spacer 22 be less than the refractive index of the lens (here—1.6 to 1.46). Once again the spacer 22, encompasses at least the aspherical lens 28, thereby eliminating any air-gap.

Figure 8:
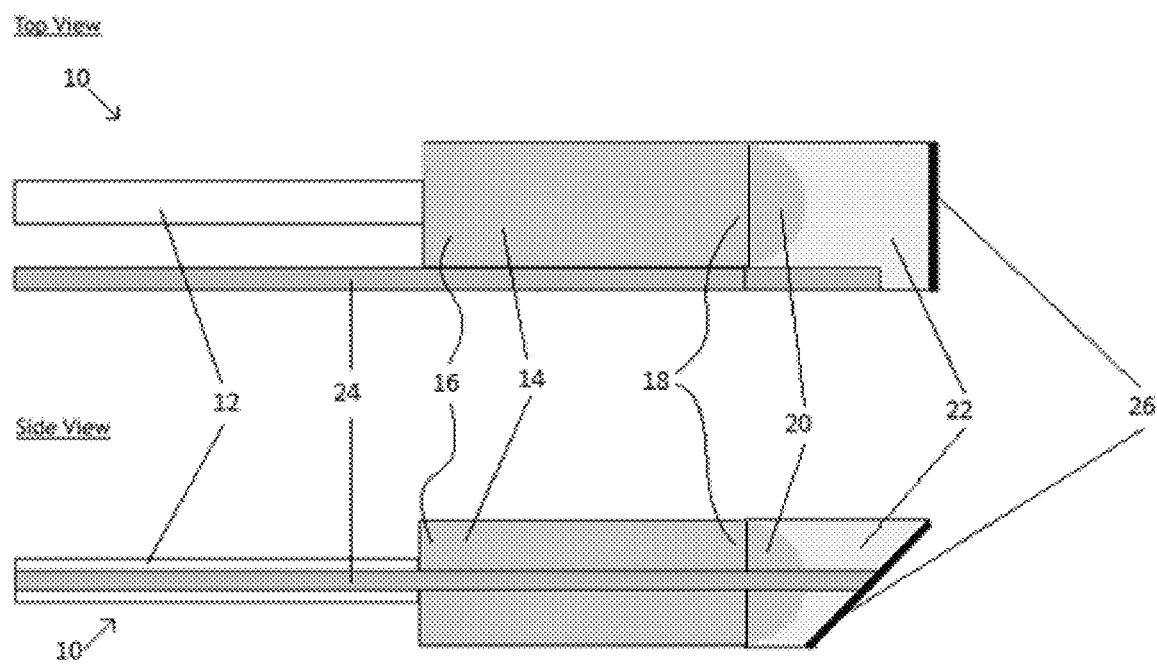
FIG. 8 provides a top and side view of a schematic diagram of an exemplary SEE probe featuring a high refractive index (e.g. sapphire) half-ball lens, according to one or more embodiments of the present subject matter.
Figure 9:
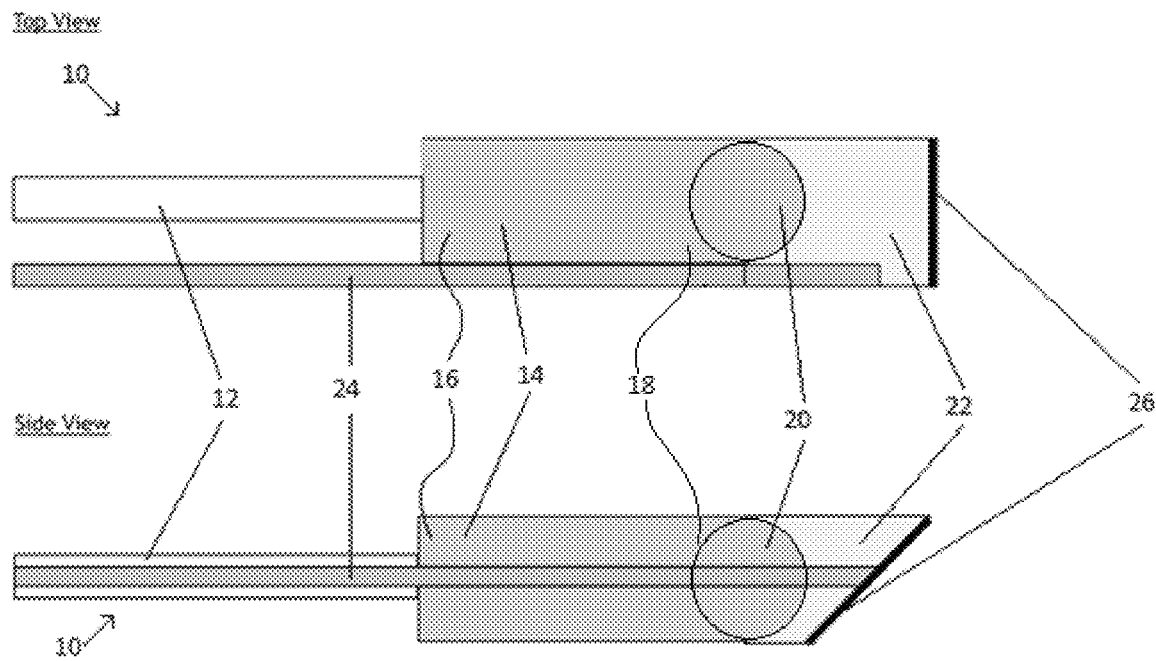
FIG. 9 depicts a top and side view of a schematic diagram of an exemplary SEE probe featuring a high refractive index (e.g. sapphire) full ball lens, according to one or more embodiments of the present subject matter.

Finally, FIGS. 8 and 9 provide schematic diagram embodiments of exemplary SEE probes 10 featuring commercially available half-ball lenses 20 or ball lenses 20, both having high refractive indexes for focusing purposes. Here, the glass rod 14 can be made with other materials if necessary. The refractive index of the glass rod 14 can be lower, equal or higher than the refractive index of the half-ball lens 20 and ball lens 20. Again, the spacer's 22 refractive index needs to be lower than the refractive index of the half-ball lens 20 or ball lens 20. As a rule of thumb, a refractive index difference of 0.1 is good for aberration correction; if possible, a larger difference of 0.2 or higher is preferred.

Figure 10:
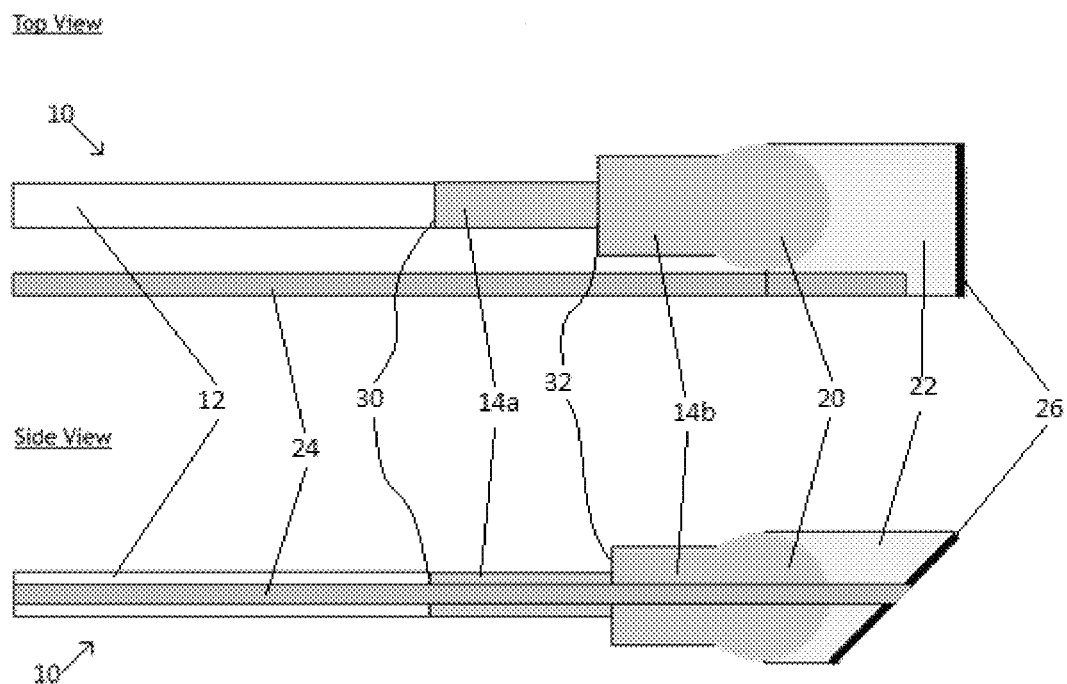
FIG. 10 provides a top and side view of a schematic diagram of an exemplary SEE probe featuring a formed ball lens from a high refractive index glass rod (e.g. sapphire), according to one or more embodiments of the present subject matter.

As mentioned in previous embodiments, it may be beneficial to splice two parts (light guiding component, rod, spacer, lens, etc.) with the same material and the same diameter. It is less preferable to splice two parts with the same material and different diameters or two parts with the same diameter but made of different materials. It is least preferred to splice two parts with different materials and different diameters. As a solution to this preference, embodiments similar to the design depicted in FIG. 10 can be useful if this dissimilarity turns out to be an issue in fabrication. As shown in FIG. 10, the light guiding component 12 (e.g. SMF, made of silica glass with doping) is first spliced 30 to a glass rod 14a of a different material and the same diameter. The first glass rod 14a is then spliced 32 to a second glass rod 14b with a larger diameter but of the same material as the first glass rod 14a. Then a ball lens 20 is formed at the tip of second glass rod 14b. This method creates an extra splice in the system, however, structural integrity is improved by this additional step. If necessary, we can also introduce the coreless fiber between the light guiding component 12 and the first glass rod 14a to minimize the refractive index differences due to the doping.

Figure 11:
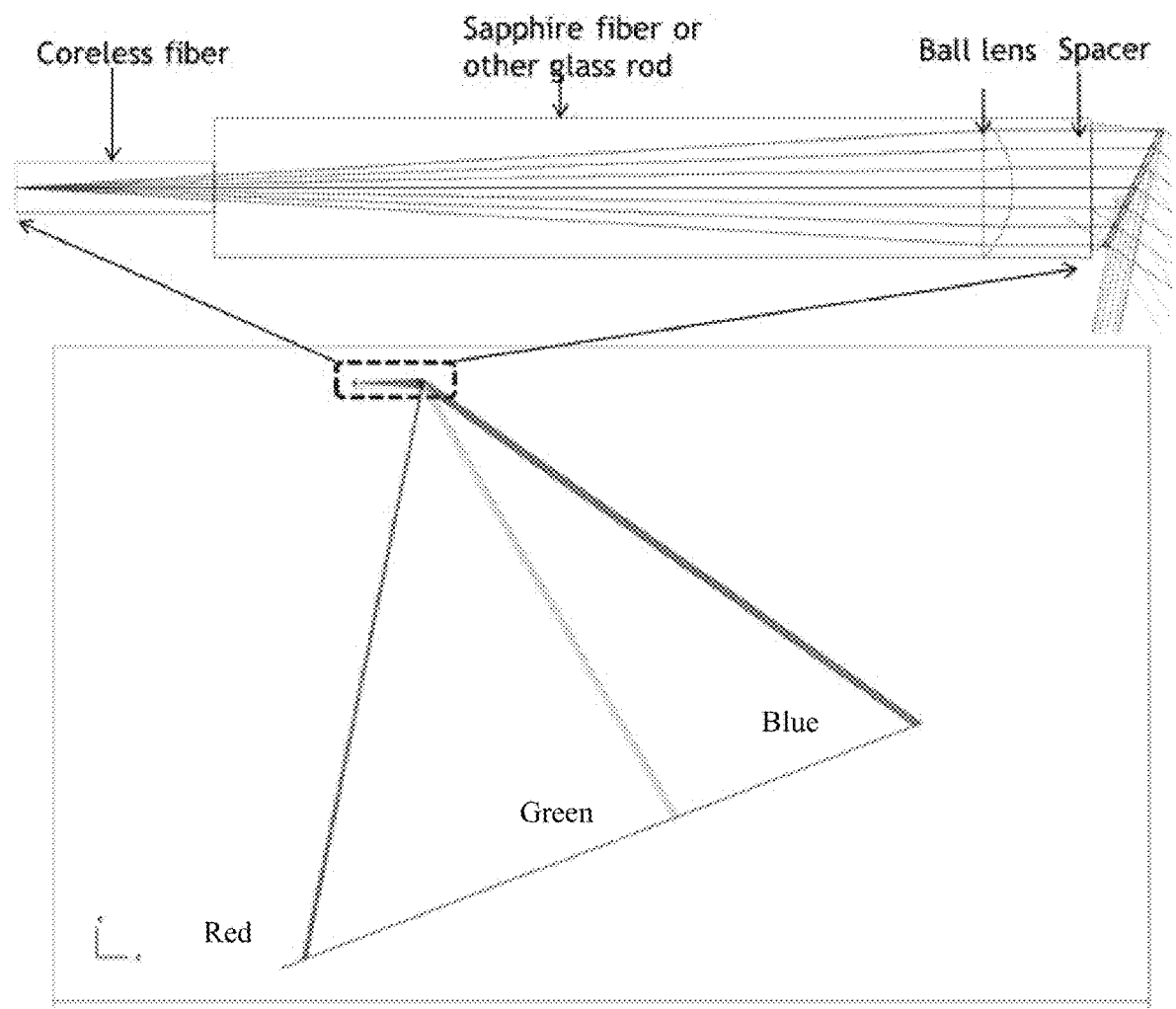
FIG. 11 illustrates an exemplary chart for optimizing an exemplary SEE probe, according to one or more embodiments of the present subject matter.

FIG. 11 provides a schematic for optimization of the monolithic design of the SEE probe shown in FIG. 5. During optimization, we introduce variables including the ball lens radius and the image plane tilt angle. The refractive index for the spacer is assumed to be 1.556 (@589 nm). If the refractive index for the ball lens is 1.6, the optimized radius is r=248 µm. This radius r will increase to 438 µm if a higher refractive index of 1.77 is assumed for the ball lens. A larger radius leads to smaller spherical aberrations, which is very beneficial. Of particular interest is the refractive index of 1.77, as this corresponds with sapphire, a premium material which can be grown into fibers with different diameters. The sapphire fiber can be later spliced to normal silica fibers. The particular advantages in sapphire fiber include sapphire's distinct features, including a higher melting point and ability to withstand harsh environment encountered in difficult situations. This is supported in sapphire's prominent use as fiber sensors for high-temperature—sensing applications. However, sapphire fibers are relatively expensive and have a high optical attenuation. Thus for the sensing industry, the signal from sapphire fiber is later coupled into a normal silica fiber for transmission, significantly reducing cost. There is a huge push in this area and great success has been achieved in the last decade (See: Adam E. Barnes, Russell G.

May, Sridhar Gollapudi, and Richard O. Claus, "Sapphire fibers: optical attenuation and splicing techniques", Applied Optics, Vol. 34, pp. 6855-6858, 1995). Besides the well-studied splicing conditions shown, it is also possible to order commercially available machines to splice the sapphire and silica optical fibers (See: "OFS announces successful splice of sapphire and silica optical fibers", Feb. 5, 2013), which further validates the present subject matter. http://www.prnewswire.com/news-releases/ofs-announces-successful-splice-of-sapphire-and-silica-optical-fibers-189784631.html].

Additionally, the cost for pure sapphire fiber, due to its wide use in laser welding systems, has been reduced substantially in the last decade. Single crystal sapphire fibers can be grown using the laser-heated pedestal growth method (LHPG) (See: G. N. Merberg and J. A. Harrington, "Optical and mechanical properties of single-crystal sapphire optical fibers," Appl. Opt., 32, 18, 3201 (1993).) and (See: D. H. Jundt, M. M. Fejer, and R. L. Byer, "Characterization of single-crystal sapphire fibers for optical power delivery systems," Appl. Phys. Lett., 55, 21, 2170 (1989)). The fibers are grown by dipping an oriented single-crystal seed into a molten droplet produced above a feed rod by laser heating. By carefully controlling the ratio of the speeds at which the source rod is pushed into the molten zone and the fiber is pulled out, a reduction ratio of source rod to fiber diameter of 3-4 is typically obtained. The sapphire fibers are grown in air at a speed of about 5 mm/min. The cross section of the c-axis fibers is roughly circular with slight deviations reflecting the trigonal symmetry. Longer fibers are grown by using a two-step reduction. A fiber grown from an approximately 1 mm diameter source rod is used as the source material to grow 100 to 150 µm diameter fibers as long as 3 m. The fibers grown are unclad (core index=1.78) and are therefore highly multimode. Despite the large numerical aperture, the measured modal power distribution after propagating a laser beam through a 0.7 m long fiber has a full angle at half intensity of only 11° [See: supra], only weakly sensitive to bends in the fiber and input launching conditions.

Figures 12A, 12B:
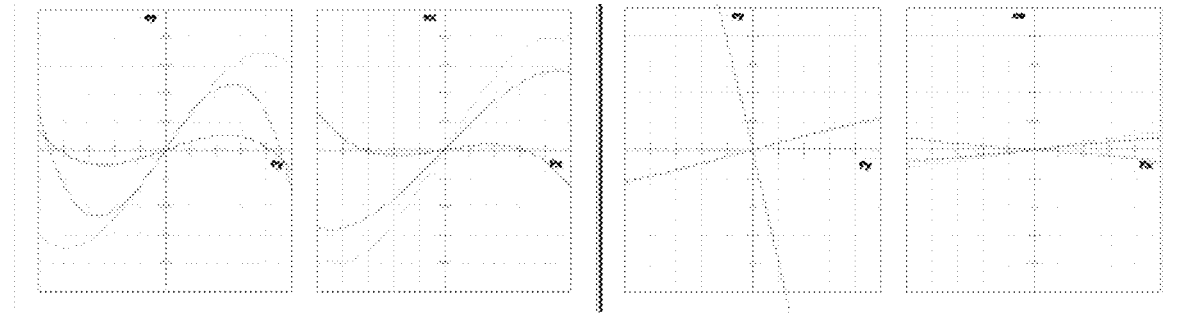
FIGS. 12(a) and 12(b) provide a pair of charts comparing image quality of an exemplary SEE probe with a contemporary GRIN lens, according to one or more embodiments of the present subject matter.

FIGS. 12(a) and 12(b) provide a pair of charts comparing image quality between the sapphire ball lens design (FIG. 12(a)) and the GRIN lens design (FIG. 12(b)). As one can see, the GRIN lens shows well-balanced aberrations for the 618 nm wavelength but the aberrations for both 415 nm and 820 nm are out of control (field of curvature is the limiting aberration here), while the aberrations for the sapphire lens are consistent and well-balanced from blue to red.

There are several ways to fabricate the ball lens design detailed in FIGS. 5-10. Here are some variants for fabrication. Option1: splice the sapphire fiber to the SMF first, and then form a ball lens at the sapphire fiber end. Option2: form a ball lens at the sapphire fiber end first, and then splice the sapphire fiber to the SMF. Both Option 1 and 2 will provide better reliability due to the spliced joint. Option3: purchase a separate sapphire half ball lens and glue the sapphire ball lens to the glass rod. The cost of the half ball lens is around 30% of the GRIN lens. Now the ball lens joint becomes the weakest link. Commercially available sapphire half-ball lenses may be purchased with different diameters (from 0.4 mm to 1 mm). It is also possible to purchase half ball lenses and ball lenses made of other materials including N—LaSF9 (n=1.85), S—LAH79 (n=2.0), etc.

Figure 13:
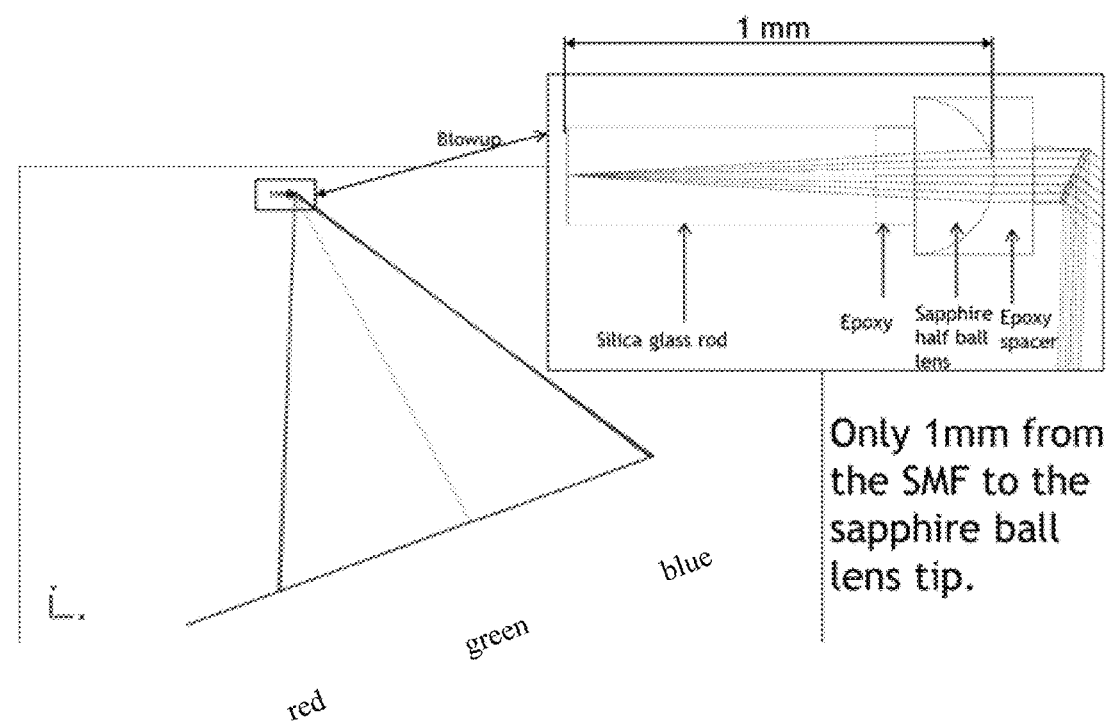
FIG. 13 provides a simulation of an exemplary SEE probe incorporating a sapphire half-ball lens, according to one or more embodiments of the present subject matter.

FIG. 13 provides the optical modeling of one embodiment of the subject SEE probe corresponding to option 3 outlined above, and visualized in FIG. 8. As one can see, it is only 1 mm from the SMF tip to the sapphire ball lens tip. As a comparison, the GRIN lens itself is rigid and has a length of several millimeters depending on the pitch of the GRIN lens. The corresponding rigid portion of the subject SEE probe, is much shorter compared to that of the GRIN lens design, which allows for far greater flexibility and maneuverability within a subject cavity. Because the sapphire fiber is very flexible, even this 1 mm embodiment may be shortened down to just the stiff sapphire half-ball lens. This can be a significant advantage if a flexible tip is necessary to investigate small corners inside the human body. In order to shorten the rigid portion of the GRIN lens design, it is possible to have a higher focusing power GRIN lens. However, a shorter GRIN lens will be harder to handle and to polish. It would also dictate larger aberrations, leading to a dissatisfactory image.

Figure 14A:
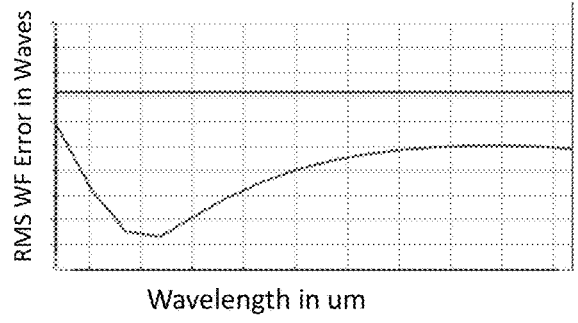
FIGS. 14(a) and 14(b) provides a pair of charts comparing image quality of an exemplary SEE probe lens incorporating a sapphire half-ball lens with a contemporary GRIN lens, according to one or more embodiments of the present subject matter.
Figure 14B:
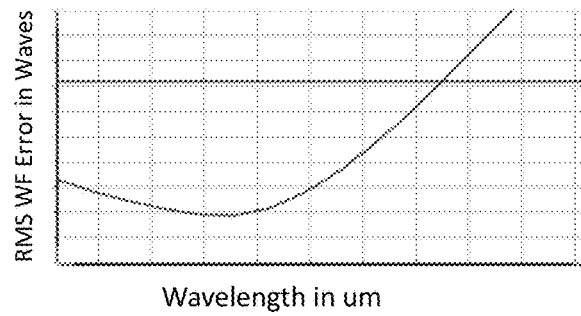

Another advantage for the sapphire half-ball lens design is its better imaging quality. As a comparison, the two graphs in FIG. 14 show the image quality for sapphire half ball lens in comparison to a GRIN Lens. As one can see, the half ball lens is superior in quality when compared to the GRIN lens for most of the wavelengths. The cost for the half-ball lens is also significant lower. In this specific embodiment, we tried to optimize the imaging quality toward the Green channel (617.5 nm) and the Red Channel (780 nm) and maintain a reasonable imaging quality of the blue channel (415 nm). The reason is for most of the supercontinuum lasers, light intensity is usually higher in both green, red and even near infrared ranges (e.g. 1000 nm). It is difficult to deliver a lot of power in the blue end. Another reason is green and red colors are more relevant for biological sample (e.g. tissue) imaging based on the feedback and preferences of clinicians and physicians. As a result, the subject disclosure has strived to achieve diffraction limited imaging focusing on both the green and red channels.

Figure 15:
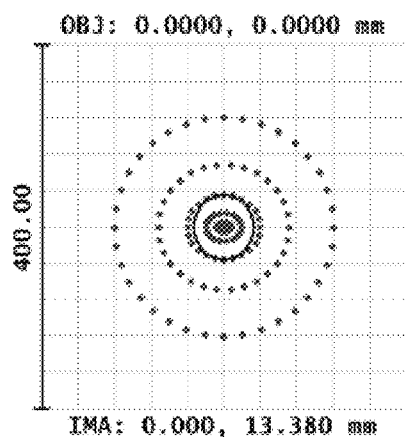
FIG. 15 provides a spot diagram for the blue channel of an exemplary SEE probe lens incorporating a sapphire half-ball lens, according to one or more embodiments of the present subject matter.
Figure 16:
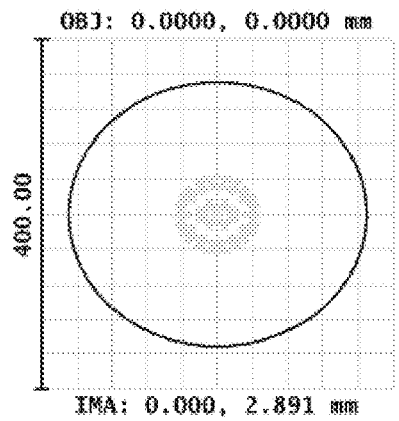
FIG. 16 provides a spot diagram for the green channel of an exemplary SEE probe lens incorporating a sapphire half-ball lens, according to one or more embodiments of the present subject matter.
Figure 17:
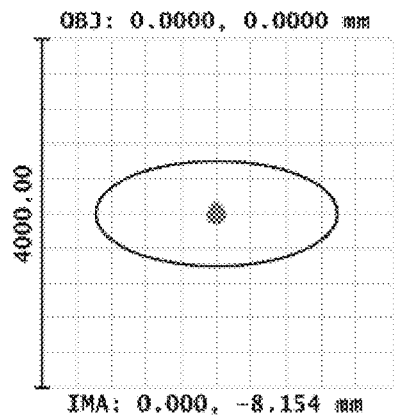
FIG. 17 provides a spot diagram for the red channel of an exemplary SEE probe lens incorporating a sapphire half-ball lens, according to one or more embodiments of the present subject matter.

The emphasis and variances of the three color channels are provided in spot diagrams for each color illustrated in FIG. 15 for the blue channel, FIG. 16 diagram for the green channel, and FIG. 17 for the red channel. As the RMS radius for green and red channel is much smaller than the Airy disk radius, the diffraction limit imaging quality is obtained for both channels. The RMS radius for blue channel is close to the Airy radius, which shows the color aberration is well balanced for the ball lens design.

During one method of fabricating the apparatus as described herein, after the glass rod is spliced to the SMF (same material, different diameters) first and cleaved to a nominal length (1.17 mm for this particular example), the image quality is checked. Then a small amount of epoxy is applied to the tip of the glass rod to pick up the sapphire half-ball lens sitting on the gel pad. If the ball lens is not centered, it is possible to use the 5 axis stage to poke it for fine adjustment. As it is sometimes necessary, to reinforce the joint between the ball lens and the glass rod, additional epoxies may be added. Then the heat shrink tube is put on the light guiding component together with the detection fiber (not shown here). As mentioned earlier, the use of spacer epoxies allows the ball lens to be encompassed with the material, thus eliminating any air-gaps which could complicate refractive index variables, as well as impair image quality.

Epoxy is then ejected into the space to encompass the whole tube with spacer epoxy. As there is space between the heatshrink tube and the fiber, the spacer epoxy can pass the ball lens and cover a long distance from the distal end via the capillary effect. After the epoxy is cured, the ball lens is fully encompassed in the spacer epoxy for enhanced mechanical strength. This embodiment of ball lens now fully mimics the GRIN lens if it is fully immersed in the epoxy, without the limitation inherent to a GRIN lens. The probe is now ready for final polishing.

If the epoxy between the glass rod and sapphire half ball is not very viscose, it is possible the ball lens will be self-centered without the need for alignment. UD1355 is a possible epoxy for such self-assembly. The viscosity of UD1355 is 447 cPs. As a comparison, OG142-112 is a little too viscose with the viscosity of 1200 to 1700 cPs.

FIGS. 18(a) and 18(b) provides a schematic diagram of an exemplary SEE probe featuring a shared ball lens utilized for color imaging, according to one or more embodiments of the present subject matter. As depicted herein, it is also possible to have a shared ball lens 20 configuration as shown in FIGS. 18(a) and 18(b). One reason for a shared ball lens 20 embodiment is for handling purposes. A larger ball lens 20 is more readily available and can be handled easily. This becomes important if one has several channels present at the same time. One of such demanding applications is for color imaging. The ball lens 20 can be injection molded if needed. The curved surface of the ball lens 20 can even face toward the light guiding component 12 as shown in FIGS. 19(a)-19(c). If the injection molding works, it is possible to mold the ball lens 20 or aspherical ball lens 28 (See FIG. 7) surface together with the grating 26 at the same time. The refractive index of the ball lens 20 should be larger than that of the spacer 22. The spacer 22 is used to glue the molded part to detection fiber 12.

Figure 21:
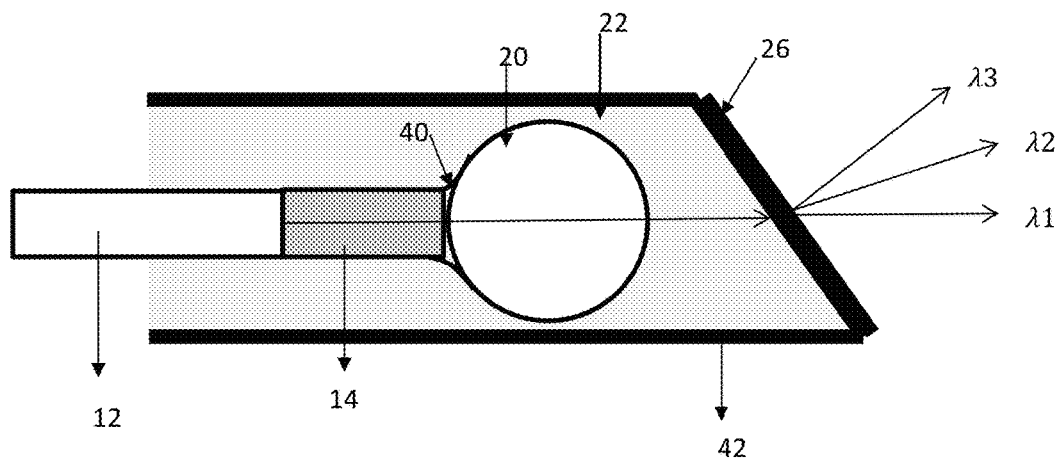
FIG. 21 depicts a schematic diagram of an exemplary forward view SEE probe.

FIG. 21 illustrates a partially-cutaway view of an example embodiment of an optical probe. In this embodiment, the probe has forward view. The optical probe includes a first light guiding component 12, a second light guiding component 14, a ball lens 20, a tube 42 filled with epoxy or other adhesive and a grating 26. The first light guiding component 12 can be, for example, a single mode fiber. The second light guiding component 14 can be, for example, a fused silica coreless fiber, a glass rod, a sapphire coreless fiber or sapphire rod. The ball lens 20 is attached to the second light guiding component 14 by epoxy 40. A tube 42 is placed over the ball lens 20 and then the tube 42 is filled with epoxy 22. Although many type of ball lens can be used, a higher refractive index of ball lens (e.g. a sapphire ball lens) may produce better optical performance. For one method of manufacture, the epoxy-filled tube 42 is angle polished and then a grating 26 is manufactured on the angle polished surface. The optical probe can be combined with a grating such as those disclosed in U.S. Pat. application Ser. No. 15/649,310, herein incorporated by reference in its entirety. The grating disperses the broad spectrum light such that at least the light path of one wavelength is parallel to the optical axis (o degree view angle). The probe with such grating produces forward view.

In other exemplary embodiments, the ball lens 20 is formed from shaping an endo of the second light guiding component 14. The ball lens 20 can also be formed by using the material (e.g., a fused-silica coreless fiber, a glass rod, a sapphire coreless fiber, a sapphire rod) into the ball lens by fusion splicing, and the first light-guiding component is spliced to the other end of the second light-guiding component.

Figure 22:
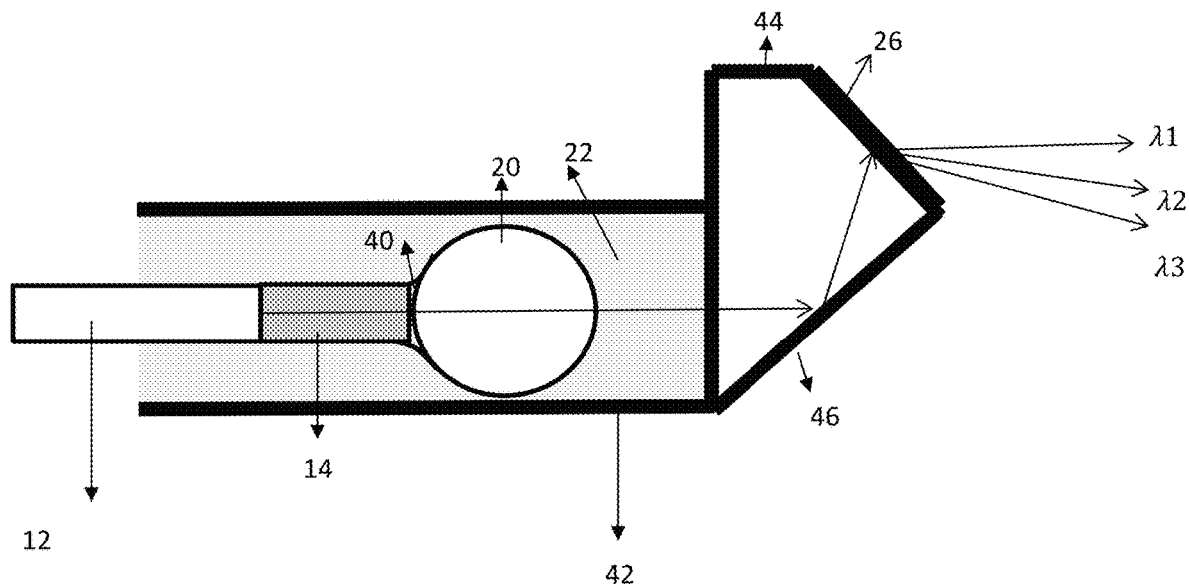
FIG. 22 depicts a schematic diagram of an exemplary SEE probe, incorporating a grating and a mirror.

FIG. 22 illustrates a partially-cutaway view of an example embodiment of an optical probe. In this embodiment, the probe has forward view and can produce either monochromatic or color image. The optical probe includes a first light guiding component 12, a second light guiding component 14, a ball lens 20, a tube filled with epoxy or other adhesive, a spacer and a grating. The first light guiding component can be single mode fiber. The second light guiding component 14 can be fused silica coreless fiber, a glass rod, a sapphire coreless fiber or sapphire rod. The ball lens 20 is attached to the second light guiding component 14 by an epoxy spacer 40. A tube 42 is placed over the ball lens 20 and then the tube is filled with epoxy. Although many type of ball lens can be used, a higher refractive index of ball lens (e.g. a sapphire ball lens) may produce better optical performance. The epoxy-filled tube 42 is attached to a spacer 44 which has two angle polished surfaces. The first surface 46 produce TIR and a grating 26 is manufactured on the upper ($2^{nd}$) angle polished surface of the spacer.

In some embodiments, the spacer 44 configuration and grating 26 are described in the probe disclosed in U.S. patent application Ser. No. 15/649,310, herein incorporated by reference in its entirety. In these embodiments, the grating 26 disperses the broad spectrum light such that the optical probe can produce forward viewing color image.

In yet other embodiments, the spacer 44 configuration and grating 26 can are described in the probe disclosed in U.S. Pat. Pub. 2016/0341951 (monochromatic forward view), such that the optical probe produces monochromatic forward viewing image.

Also for example, in some embodiments, the ball lens 20 is formed from shaping an endo of the second light guiding component 14. The ball lens 20 can also be formed by using the material (e.g., a fused-silica coreless fiber, a glass rod, a sapphire coreless fiber, a sapphire rod) into the ball lens by fusion splicing, and the first light-guiding component 12 is spliced to the other end of the second light-guiding component 14.

The molding of the grating is always an integrated part of the ball lens design. PDMS (silicone) has been demonstrated for its capability for molding fine gratings (See: Dongkyun Kang, Ramses V. Martinez, George M. Whitesides and Guillermo J. Tearney, "Miniature grating for spectrally-encoded endoscopy", Lab on a chip, 13, pp 1810-1816, 2013). The following steps outline the procedure for assembling the ball lens with molded gratings. First, immerse the ball lens into a cylinder full of PDMS; one side of PDMS is in contact with the grating surface; cure the PDMS with heat afterwards. The cylinder can be a two piece mold for easier mold release. The cylinder can also be part of the protective support which is designed to protect the illumination core. It is possible to mold another curvature on the distal end of the probe for better aberration correction; it is also possible to directly mold the grating inside the heat shrink tube.

A sacrificial layer or tube made of Teflon can be introduced in the molding process to decrease the diameter of the molded part. If Teflon or other non-sticky material is used, the tube initially used in the epoxy (or other spacer material) injection process can be peeled off after the material is cured (either thermally or UV cured). If the light guiding component is off-center with regard to the ball lens (e.g. the designs shown in FIGS. 18(a)-(b) and 19(a)-(c)), the light coming out of the ball lens will be off-centered as well.

It is possible to improve the imaging quality further. The key is to decrease the curvature of the ball lens. The focal length of the ball lens can be calculated as:

$$f = \frac{R}{n_b - n_s}$$

where R is the radius of the ball lens, $n_b$ and $n_s$ are the refractive indexes of the ball lens and the spacer respectively. In order to achieve the same focusing power while having a larger radius R, it is necessary to increase the refractive index differences between the ball lens and the spacer. Flint glass or sapphire glass (1.77) can be used. It is also possible to have aspheric the lens made from polycarbonate. As we are able to choose different materials for the spacer, it is possible to improve the design flexibility to achieve different working distances by varying the matching refractive index.

Generally speaking, a refractive index difference of 0.1 is good for aberration correction; if possible, a larger difference of 0.2 or even 0.3 and higher is advantageous for better performance. In one embodiment we achieved diffraction limited imaging with a larger aperture by using sapphire half ball lens (n=1.77) and silicone (n=1.41) as the spacer. The refractive index difference here is as high as 0.36. Certain silicones (e.g. the one offered by Gelest) can have a lower refractive index of 1.39 (Gelest OE39). Furthermore, some glass materials may also feature a very high refractive index, some even higher than that of sapphire. A couple examples include N—LaSF9 (n=1.85) and S—LAH79 (n=2.0).

A lower refractive index difference does not mean the disclosure provided herein will not function as intended. One example is the embodiment shown in FIG. 11, wherein the refractive index of the ball lens is approximately 1.6 and that of spacer is approximately 1.556. This design results in a smaller radius of the ball lens which in sequence introduces larger aberration. Depending on how the design is made, a smaller radius may also cause issues for handling and fabrication as the ball lens will be much smaller.

Figure 2:
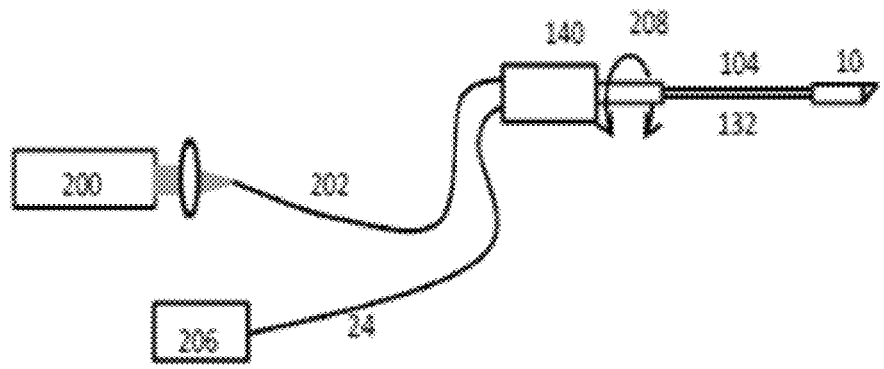
FIG. 2 provides a diagram of a system using an exemplary SEE probe, according to one or more embodiments of the present subject matter.

A system to acquire the image from the SEE probe according to an exemplary embodiment of the present disclosure is shown in a diagram of FIG. 2. For example, a light source 200 outputs light of broadband spectrum (or other electro-magnetic radiation). The range of the wavelength can cover most the visible region and some near infrared region, which is from 400 nm through 800 nm. However, other wavelengths may also be used. In the exemplary imaging system, the light can be directly guided or otherwise provided into a light guiding component 202, which can be a light guiding component. The light guiding component 202 can pass through a hollow core motor 140, after which the exemplary probe 10 is attached. The light scattered back from the sample (e.g., tissue) can be collected by a detection fiber 24. The detection fiber 24 can be connected to a detector 206 in which the intensity of selected wavelength can be detected. This exemplary function can be performed by, e.g., a spectrometer.

Figure 3:
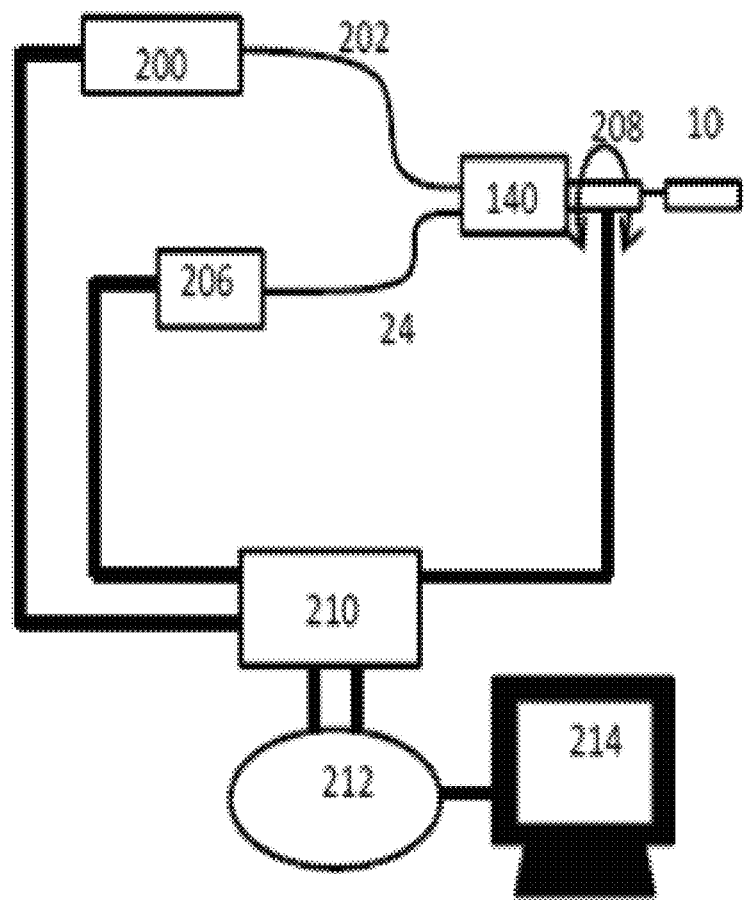
FIG. 3 illustrates a diagram of a system using an exemplary SEE probe, according to one or more embodiments of the present subject matter.

FIG. 3 shows a diagram the imaging system according to another exemplary embodiment of the present disclosure. This exemplary imaging system can be used with, for example, one or more exemplary probes as described in various exemplary embodiments herein. To operate the exemplary imaging system of FIG. 3, a user (e.g., a doctor, nurse, or technician) can connect the exemplary SEE probe 10 having a fixed guiding portion and a rotatable dispersive portion connected to a hollow core motor 140. A computer unit/arrangement 210 can be connected to the light source 200 and to the detector 206. It may also be connected to the hollow core motor 140 (connection not shown).

In some embodiments, the detection fiber 24 could be fixed, i.e. not rotating but the light guiding component 202 may be rotated. Further, the light guiding component 202 could be connected to a rotary joint (not shown here) so that the probe tip could rotate continuously in one direction.

A command can be transmitted to the computer unit/arrangement 210 via a user interface unit/arrangement 212.

A touch panel screen can be includes as part of the user interface unit/arrangement 212, but key board, mouse, joystick, ball controller, and foot pedal can also be included with the user interface unit/arrangement 212. The user can cause a command to be initiated to observe inside the human body through the exemplary SEE probe using the user interface unit 212. For example, when the user inputs a command, the command is transmitted to the central processing unit for execution thereby.

The computer unit/arrangement 210 can include a central processing unit (CPU), memory, input/output interface, detector interface, and/or data storage/RAM. In the data storage, software which configures the central processing unit to perform the determinations and various functions for the user to operate the imaging system can be pre-installed. Computer unit/arrangement 210 may comprise other devices as well. The CPU is configured to read and perform computer-executable instructions stored in the Storage/RAM. The computer-executable instructions may include those for the performance of the methods and/or calculations described herein. For example, CPU calculates positional information based on the spectral information from the probe. Storage/RAM includes one or more computer readable and/or writable media, and may include, for example, a magnetic disc (e.g., a hard disk), an optical disc (e.g., a DVD, a Blu-ray), a magneto-optical disk, semiconductor memory (e.g., a non-volatile memory card, flash memory, a solid state drive, SRAM, DRAM), an EPROM, an EEPROM, etc. Storage/RAM may store computer-readable data and/or computer-executable instructions. The components of the computer unit/arrangement may communicate via a bus. The I/O interface provides communication interfaces to input and output devices, which may include a display 214, and/or other devices including a keyboard, a mouse, a printing device, a touch screen, a light pen, an optical storage device, a scanner, a microphone, a camera, a drive, communication cable and a network (either wired or wireless). The detector interface may also provide communication interfaces to input and output devices, which may include CMOS sensor, CCD sensor, photomultiplier tube (PMT), an avalanche photodiode detector (APD), etc.. Also, the function of detector may be realized by computer executable instructions (e.g., one or more programs) recorded on a Storage/RAM.

The computer unit/arrangement 210 can be programmed to apply exemplary image processing such as noise reduction, coordinate distortion correction, contrast enhancement and so on. After or even during the image processing is performed, the data can be transmitted from the computer unit/arrangement 210 to a display 214. In some exemplary embodiments, a liquid crystal display or an OLED display can be the display 214. The display 214 can display, for example, the image obtained by the line scan according to various exemplary embodiments of the present disclosure. The display 214 can also display other information than the image, such as the date of observation, what part of the human body is observed, the patient's name, operator's name and so on.

According to certain exemplary embodiments of the use of the SEE probe 10 as described herein, the computer unit/arrangement 210 can then transmit another command to the hollow core motor 140. With this command, the hollow core motor 140 is caused by the computer unit/arrangement 210 to rotate the rotatable dispersive portion of the SEE probe by predetermined amount $\delta\theta$ around the reference axis. After the rotation, the line scan can be considered to be completed, the image data can be sent to the display 214, to be displayed (i.e., with the information regarding the rotation by $\delta\theta$). Repeating this step can provide a two-dimensional image.

The detector interface also provides communication interfaces to input and output devices, which may include CMOS sensor, CCD sensor, photomultiplier tube (PMT), an avalanche photodiode detector (APD), etc. Also, the function of detector may be realized by computer executable instructions (e.g., one or more programs) recorded on a Storage/RAM.

In one exemplary operation, the user can place the exemplary SEE probe into a sheath, and then can insert such arrangement/configuration into a predetermined position of a human body. The sheath alone may be inserted into the human body in advance, and it is possible to insert the SEE probe into the sheath after sheath insertion. The exemplary probe can be used to observe inside human body and works as endoscope such as arthroscopy, bronchoscope, sinuscope, vascular endoscope and so on.

In various embodiments, the subject SEE probe may be configured for color imaging. In such embodiments, the SEE probe may be configured to allow multiple orders of spectrally dispersed light to exit the grating component at substantially the same angle. For example, the $3^{rd}$, $4^{th}$ and $5^{th}$ orders; the 4th, $5^{th}$, and $6^{th}$ orders; or the $5^{th}$, $6^{th}$, and $7^{th}$ orders of spectrally dispersed light exit the grating component at substantially the same angle. Disclosure of this color imaging embodiment is provided in U.S. patent application Ser. No. 15/418,329, titled "Spectrally Encoded Probes Having Multi-Diffraction Order", which is incorporated by reference, in its entirety, herein.

Figure 4:
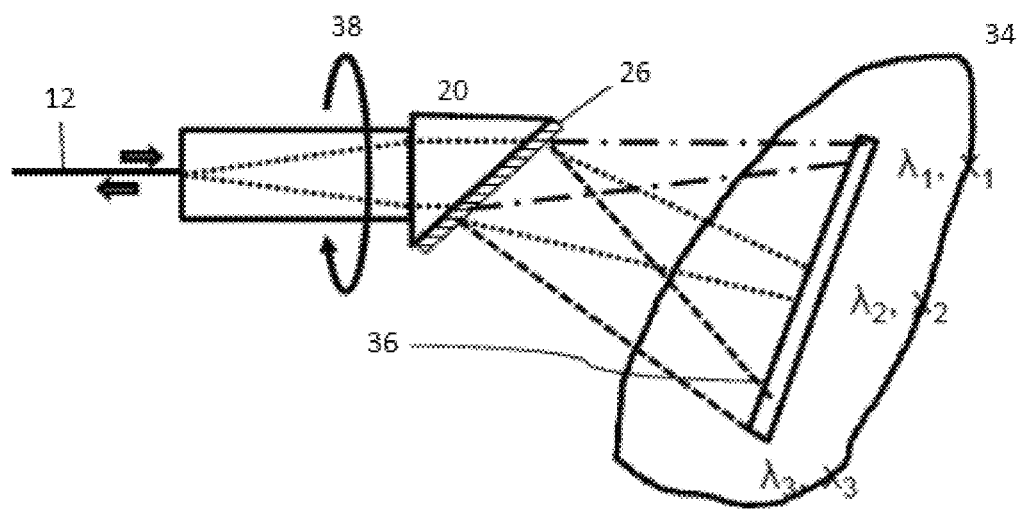
FIG. 4 depicts an exemplary SEE probe incorporating a diffraction grating, according to one or more embodiments of the present subject matter.

Further embodiments may incorporate advance diffraction grating elements for broader use of the SEE probe. FIG. 4 provides diagram of an exemplary SEE probe according to an exemplary embodiment of the present disclosure, utilizing advance grating. This exemplary SEE probe can include a light guiding component 12, a ball lens 20, and a diffraction grating 26. Broadband light (or other electro-magnetic radiation) can be coupled or otherwise provided into the fiber 12, and focused by the lens 20. The light (or other electro-magnetic radiation) travels through the lens 20 and is incident on the grating 26 where it is diffracted by the grating component 26. Each light (having a wavelength $\lambda$ or a wavelength band) is focused on a unique spatial location on the sample 34, as shown in FIG. 4 as $X_1$, $X_2$, and $X_3$ for wavelengths $\lambda_1$, $\lambda_2$, and $\lambda_3$. Therefore, the light (or other electro-magnetic radiation) can be focused into a line 36 (shown as spectrally-encoded line in FIG. 4), rather than onto a point. One of the wavelengths in the light can propagate parallel to the optical axis of the lens, shown as $\lambda_1$ shown in FIG. 4. Light (or other electro-magnetic radiation) reflected by the sample 34 can be coupled or otherwise provided back to the fiber 12 or to a different fiber (not shown) and then can be delivered to a detector that includes a spectrometer (not shown). At the spectrometer, the spectrum of the returning light (or other electro-magnetic radiation) can be read out, which can be used to generate a line image of the sample using a computer or other processor (not shown). The exemplary SEE probe can be scanned rotationally along the optical axis of the lens as shown by the arrow 38, e.g., by rotating or oscillating the lens 20 or in other ways which should be understood to those having ordinary skill in the art.

In addition, the field of view of the probe may be enhanced and/or expanded by incorporating a rotating probe. In such an embodiment, the probe or parts thereof may be rotated or oscillated as indicated by the arrow. For example, the light guiding component may be rotated via a rotary junction. In addition, the detection fiber may optionally be rotated along with the light guiding component, or the light guiding component may be stationary in comparison to the detection fiber. If rotated, the detection fiber may be connected, via a rotary junction, to a second detection fiber.

The probe in FIG. 4 may be rotated around the optical axis by a motor as indicated by the arrow 38 such that illumination light lines scan the sample, and 2D data (spectrum and time) can be obtained by the spectrometer. The motor can be, for example, a Galvano motor, stepping motor, DC motor, etc. A rotary junction may be used for rotation of the probe. For example, by rotating the spectrally encoded lines in the direction of the arrow, a circular region can be imaged. This circular region can be located approximately perpendicular to the SEE probe, and therefore, the exemplary SEE probe shown in FIG. 4 can conduct forward-view imaging. Alternatively, the probe may be oscillated to provide similar 2D data. At the spectrometer, the spectrum of the collected light can be read out, which can be used to generate a line image of the sample 34.

This and other advance grating elements are provided in U.S. patent application Ser. No. 15/649,310 titled "Spectrally Encoded Probes", incorporated by reference herein, in its entirely.

The ball lens design disclosed here may be combined with other aspects of SEE endoscopes, probes, and methods as described, for example, in U.S. Pat. Nos. 6,341,036; 7,447,408; 7,551,293; 7,796,270; 7,859,679; 8,045,177; 8,145,018; 8,838,213; 9,254,089; 9,295,391; and Patent Application Publication Nos. WO2015/116951 and WO2015/116939, each of which patents and patent publications are incorporated by reference herein in their entireties.

Figure 20:
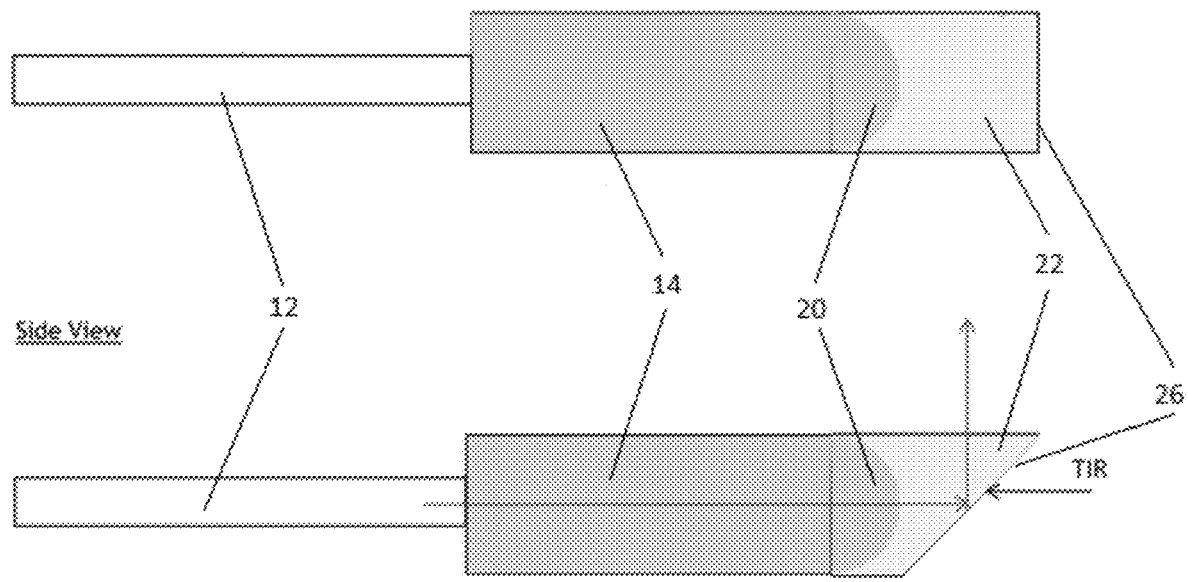
FIG. 20 provides a top and side view of a schematic diagram of an exemplary SEE probe incorporating a sandwiched ball lens for OCT applications, according to one or more embodiments of the present subject matter.

The ball lens design disclosed here describes a fundamental focusing element. It can be used for other applications such as Optical Coherence Tomography ("OCT") as shown in FIG. 20. Without the grating, the light that passes the ball lens will hit the angle polished spacer and then be reflected by total internal reflection or a reflective coating. If the illumination fiber is off-centered in regard to the ball lens (e.g. the designs shown in FIGS. 18-19), the light coming out of the ball lens will be off-centered as well. Exemplary OCT probes, methods, and systems that may be used with the ball lens described herein are disclosed in U.S. Pat. Nos. 7,872,759; 8,289,522; and 8,928,889 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942 and U.S. Patent Publication Nos. 2010/0092389, 2012/0101374 and 2016/0228097, each of which patents and patent publications are incorporated by reference herein in their entireties.

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

The invention claimed is:

1. An apparatus for endoscopy comprising:
   a probe for illuminating a sample, comprising:
      a light guiding component for guiding an illumination light;
      a light focusing component;
      a spacer; and
      a dispersive component, and
   a detection fiber for detecting light from the sample;
   wherein the spacer is configured between the dispersive component and the light focusing component, and
   wherein the light focusing component is a ball lens and the spacer at least partially encompasses the ball lens.

2. The apparatus according to claim 1, wherein the spacer has a refractive index less than a refractive index of the light focusing component.

3. The apparatus according to claim 1, further comprising:
   a rod situated between the light guiding component and light focusing component, such that the rod is configured to expand light from the probe.

4. The apparatus according to claim 3, wherein the refractive index of the rod is equal to or higher than a refractive index of the light guiding component.

5. The apparatus according to claim 3, wherein the rod diameter is equal to or greater than a diameter of the light guiding component.

6. The apparatus according to claim 1, wherein a refractive index difference between the light focusing component and the spacer is greater than or equal to 0.05.

7. The apparatus according to claim 1, wherein the ball lens is selected from the group comprising a full-ball lens, a half-ball lens, a portioned-ball lens, a lens with a spherical surface, a lens with aspherical surface and combinations therefrom.

8. The apparatus according to claim 1, wherein the light focusing component is at least partially made of an element selected from the group consisting of, sapphire, ruby, flint glass, injection moldable glass, injection moldable plastics, high refractive index silicone, high refractive index epoxies and combinations therefrom.

9. The apparatus according to claim 1, wherein the light focusing component is at least partially formed by an injected molded lens of spherical or aspherical shape.

10. The apparatus according to claim 1, further comprising a focusing element for focusing the apparatus by varying a refractive index of the spacer.

11. The apparatus according to claim 1, further comprising:
   a computer arrangement in communication with the apparatus, and configured to process information received from the apparatus to create an image.

12. The apparatus according to claim 1, where the spacer material is at least partially made of an element selected from the group consisting of, UV or heat cured epoxies, PDMS, PMMA, PC, injection moldable glass and combinations therefrom.

13. An apparatus for endoscopy comprising:
   a probe for illuminating a sample, comprising:
      a light guiding component for guiding an illumination light;
      a light focusing component;
      a spacer;
      at least one dispersive component; and
      at least one reflective component; and
   a detection fiber for detecting light from the sample;
   wherein the spacer is configured between the dispersive component and the light focusing component, and
   wherein the light focusing component is a ball lens and the spacer at least partially encompasses the ball lens.

14. An apparatus for optical coherence tomography or other endoscopy imaging modalities comprising:
   a probe for illuminating a sample, comprising:
      a light guiding component for guiding an illumination light;
      a light focusing component;
      a spacer; and
      a reflective component,
   wherein the spacer is configured between the reflective component and the light focusing component, and
   wherein the light focusing component is a ball lens and the spacer at least partially encompasses the ball lens.

15. The apparatus according to claim 14, wherein the spacer has a refractive index less than a refractive index of the light focusing component.

16. The apparatus according to claim 14, wherein the difference between a refractive index of the light focusing component and the spacer is greater than or equal to 0.05.

17. The apparatus according to claim 14, wherein the ball lens is selected from the group consisting of a full-ball lens, a half-ball lens, a portioned-ball lens, a lens with a spherical surface, a lens with aspherical surface and combinations therefrom.

18. The apparatus according to claim 14, wherein the light focusing component is at least partially made of an element selected from the group consisting of, sapphire, ruby, flint glass, injection moldable glass, injection moldable plastics, high refractive index silicone, high refractive index epoxies and combinations therefrom.

19. The apparatus according to claim 14, where the spacer material is at least partially made of an element selected from the group consisting of, UV or heat cured epoxies, PDMS, PMMA, PC, injection moldable glass and combinations therefrom.

* * * * *